(12) United States Patent
Johnson et al.

(10) Patent No.: US 7,236,241 B2
(45) Date of Patent: Jun. 26, 2007

(54) METHOD OF MAKING A STANDARD TOOL FOR CALIBRATING STRESS ANALYSIS MEASURING DEVICES AND A SET OF THE STANDARD TOOLS

(75) Inventors: Mary Ann Johnson, Rockport, MA (US); David W. Johnston, Kensington, NH (US)

(73) Assignee: Osram Sylvania Inc., Danvers, MA (US)

( * ) Notice: Subject to any disclaimer, the term of this patent is extended or adjusted under 35 U.S.C. 154(b) by 343 days.

(21) Appl. No.: 10/907,344

(22) Filed: Mar. 30, 2005

(65) Prior Publication Data
US 2006/0221334 A1  Oct. 5, 2006

(51) Int. Cl.
G01J 1/10 (2006.01)
G01B 11/16 (2006.01)
(52) U.S. Cl. ............ 356/243.1; 356/33; 356/364
(58) Field of Classification Search .. 356/243.1–243.8, 356/33–35, 364–369; 250/252.1
See application file for complete search history.

(56) References Cited
U.S. PATENT DOCUMENTS
4,655,589 A * 4/1987 Cestaro et al. ............. 356/35

2003/0076487 A1 * 4/2003 Cannon et al. ............. 356/33
2006/0164641 A1 * 7/2006 Russell et al. ............. 356/367

* cited by examiner

Primary Examiner—Hoa Q. Pham
(74) Attorney, Agent, or Firm—Robert F. Clark

(57) ABSTRACT

A method of making a standard tool for calibrating polarimeters that analyze stress in photoelastic material, includes the steps of partially annealing a starting piece of tempered glass so that the starting piece has a retardance below 250 nm/cm, removing a peripheral portion of the starting piece (preferably, at least about 20% of its radial dimension) to leave a working piece, cutting a rectangular parallelepiped from the working piece, polishing two opposing faces of the rectangular parallelepiped where the two opposing faces are spaced apart by a measurement distance through which light passes during stress analysis in a polarimeter, and determining a birefringence of the rectangular parallelepiped across the measurement distance using a calibrated polarimeter. The standard tool is the rectangular parallelepiped having the determined birefringence for the measurement distance. The method can be used to make a set of the standard tools with different measurement distances.

18 Claims, 1 Drawing Sheet

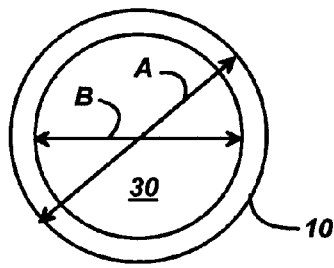
Fig. 1
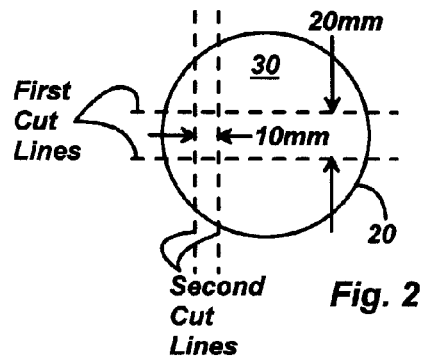
Fig. 2
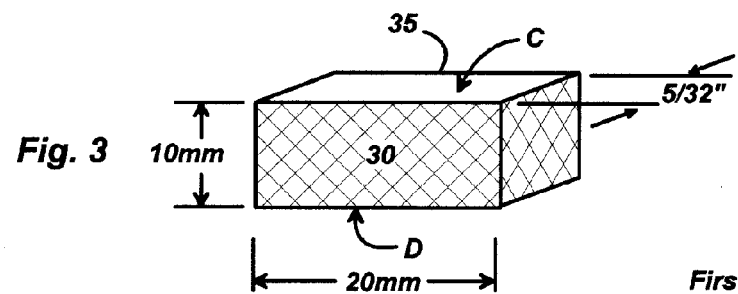
Fig. 3
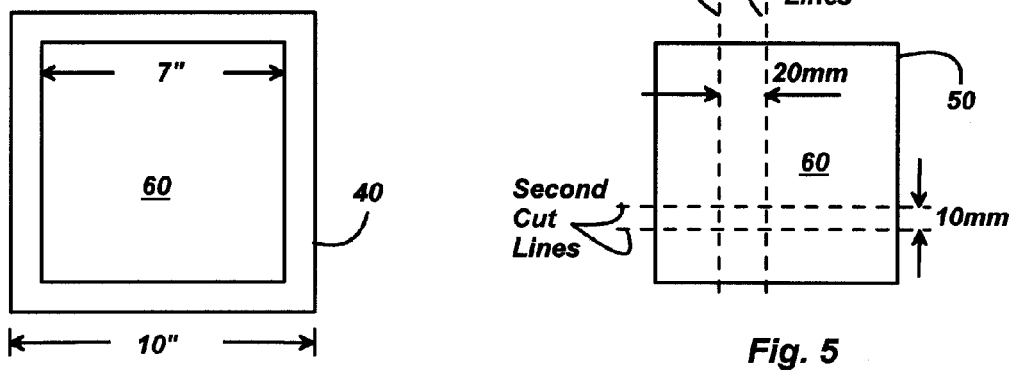
Fig. 4
Fig. 5
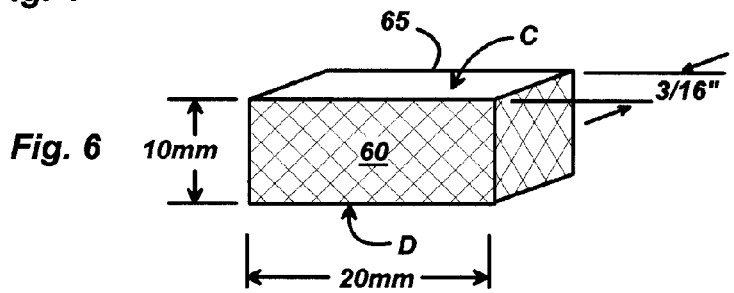
Fig. 6

METHOD OF MAKING A STANDARD TOOL FOR CALIBRATING STRESS ANALYSIS MEASURING DEVICES AND A SET OF THE STANDARD TOOLS

BACKGROUND OF THE INVENTION

The present invention is directed to a method of making a standard tool for calibrating polarimeters that analyze stress in photoelastic material, and to a set of these standard tools.

Polariscopes and polarimeters analyze stress in photoelastic materials, such as glass. Stress is viewed through a polariscope by placing a sample of the material to be analyzed in front of a polarized light source and viewing the sample though an analyzer and full wave plate. Stress in the sample appears as blue and yellow areas when the stress direction is +/−45° to the polarized light. The more intense the color, the higher the stress for samples of equal thickness.

The stress may be measured with a polarimeter by replacing the full wave plate of the polariscope with a quarter wave plate. With the analyzer set to zero degrees, stress areas appear white. The white area is viewed while rotating the analyzer and the rotation is stopped when the white area is extinguished (dark). Sample thickness affects the readings and thus the stress is recorded as the number of degrees of rotation per unit thickness.

The polarizing films in polariscopes and polarimeters degrade over time and parts of the optical systems of these devices can become misaligned, both of which compromise the accuracy of the stress analysis results. These instruments need to be checked routinely to ascertain their accuracy.

Devices exist for ascertaining the accuracy of polariscopes and polarimeters. For example, the Babinet Soleil Compensator has a variable retardation plate that cancels phase differences in birefringent materials and can be used to check the accuracy of these instruments. However, the device is expensive and delicate and the operator must be highly skilled.

Standard tools for ascertaining the accuracy of polariscopes and polarimeters that are less sophisticated than the Babinet Soleil Compensator are also known. For example, a tempered glass disk with known birefringence is available. However, retardance can vary across the surface of the disk and precise measurements of the distance from the edge of the disk are also required. Further, the disks have one stress or birefringence level and additional levels are achieved only by stacking plural disks, which can cause further errors given the tight tolerances for measurements of the distance from the disk edge.

Another problem with polariscopes and polarimeters is that training is needed to ensure accurate operation of these instruments. Samples with high birefringence exhibit chromatic aberration so that different wavelengths of light resolve at different rotations of the analyzer. An operator can see overlapping images that complicate the determination when the birefringence has been compensated by rotation of the analyzer. The operator must be taught what to see when the analyzer has been rotated the correct amount. A simple tool for facilitating this training would be particularly advantageous.

Accordingly, the prior art tools for calibrating stress analysis devices have operational and training disadvantages.

SUMMARY OF THE INVENTION

An object of the present invention is to provide a novel method of making a standard tool for calibrating devices that analyze stress in photoelastic materials that avoids the problems of the prior art.

A further object of the present invention is to provide a novel method of making a standard tool for calibrating these devices where the method provides a standard tool that facilitates device calibration and operator training.

A still further object of the present invention is to provide a novel method of making a standard tool for calibrating devices that analyze stress in photoelastic material that includes the steps of partially annealing a starting piece of tempered glass, removing a peripheral portion of the starting piece (preferably, at least about 20% of its radial dimension) to leave a working piece, cutting a rectangular parallelepiped from the working piece, polishing two opposing faces of the rectangular parallelepiped where the two opposing faces are spaced apart by a measurement distance through which light passes during stress analysis in a polarimeter, and determining a birefringence of the rectangular parallelepiped across the measurement distance using a calibrated polarimeter.

A yet further object of the present invention is to provide a novel set of these standard tools for calibrating devices that analyze stress in photoelastic materials that avoids the problems of the prior art.

These and other objects and advantages of the invention will be apparent to those of skill in the art of the present invention after consideration of the following drawings and description of preferred embodiments.

BRIEF DESCRIPTION OF THE DRAWINGS

FIG. 1 is a top view of a partially annealed tempered glass disk showing the removal of the peripheral portion.

FIG. 2 is a top view of the disk of claim 1 showing the cut lines by which the rectangular parallelepiped is formed.

FIG. 3 is a pictorial representation of a parallelepiped cut from the disk of FIG. 2 showing the two opposing faces and the marking of the remaining four faces.

FIG. 4 is a top view of a partially annealed tempered glass sheet showing the removal of the peripheral portion.

FIG. 5 is a top view of the sheet of claim 4 showing the cut lines by which the rectangular parallelepiped is formed.

FIG. 6 is a pictorial representation of a parallelepiped cut from the sheet of FIG. 5 showing the two opposing faces and the marking of the remaining four faces.

DETAILED DESCRIPTION OF THE INVENTION

For a better understanding of the present invention, together with other and further objects, advantages and capabilities thereof, reference is made to the following disclosure and appended claims taken in conjunction with the above-described drawings.

The inventive method of making a standard tool for calibrating devices that analyze stress in photoelastic material starts with a piece of tempered glass. As is known, tempering is a process that strengthens glass. Tempered glass has been heated above the glass transition temperature and rapidly cooled to build compressive stresses at the surface and tensile stress in the mid-plane. Residual stresses in tempered glass are so high that cutting or breaking the glass results in dicing (rapid and total reduction to small fragments.)

The starting piece of tempered glass, having a first thickness and a first dimension that it perpendicular to the first thickness, is partially annealed, preferably to the strain point. The partial annealing creates a lower level of stress or birefringence and creates a consistent level of retardance per unit thickness of the glass. When the retardance is kept below 250 nm/cm, the partially annealed tempered glass can be cut or polished with conventional glass working tools.

The partial annealing of the starting piece of tempered glass may include heating an oven containing the starting piece of tempered glass from ambient temperature to a first temperature range of 400-500° C. at a first rate, holding the oven temperature to within the first temperature range for a predetermined time, cooling the oven to a second temperature range of 300-400° C. at a second slower than the first rate, and then cooling the oven to ambient temperature at a third rate faster than the first rate. In preferred embodiments, the first rate is about 20° C./min, the second rate is about 5° C./min, and the third rate is about 50° C./min, and step of holding the oven temperature for a predetermined time includes holding the oven temperature at about 475° C. for 10-15 minutes.

A peripheral portion of the partially annealed starting piece is then removed to leave a working piece having the first thickness and a second dimension less than the first dimension. Preferably, the second dimension is less than 80% of the first dimension so as to provide a consistent stress value from a central portion of the starting piece.

The working piece is then cut to create a rectangular parallelepiped of desired size. The cutting step includes making first cuts at a first distance apart and thereafter making second cuts at a second distance apart perpendicular to the first cuts, the second distance defining a measurement distance through which light passes during stress analysis in a stress analysis device. The first and second distances may be selected based on a particular stress analysis device or may be nominal values that provide tools useful in various devices.

Two opposing faces of the rectangular parallelepiped are then polished, where the two opposing faces are spaced apart by the measurement distance. The two opposing faces are perpendicular to the first surface. The four remaining faces of the rectangular parallelepiped are marked to avoid using these four remaining faces when calibrating stress analysis devices.

Thereafter, a birefringence of the rectangular parallelepiped is determined across the measurement distance using a calibrated stress analysis device. The rectangular parallelepiped becomes the standard tool that has the determined birefringence for the measurement distance.

A set of the standard tools can be made by cutting further rectangular parallelepipeds from the working piece and polishing respective opposing faces thereof, where each of the further rectangular parallelepipeds has a different respective measurement distance.

These tools maintain their birefringence over time and thus are suitable standard tools for calibrating devices that analyze stress in photoelastic material. Further, the ease with which such tools with various capabilities can be manufactured facilitates their use when training operators how to use the stress analysis devices.

A first embodiment of the invention uses a soda-lime tempered lens disk 10 shown in FIG. 1 (e.g., the disk is circular and has a diameter A of 4.5 inches and is 5/32 inches thick). The disk 10 is partially annealed using the following schedule:

| Step | Ramp | Temperature |
| --- | --- | --- |
| 1 | 20° C. per minute | 460° C. |
| 2 | no hold | 460° C. |
| 3 | 5° C. per minute | 475° C. |
| 4 | hold 10 minutes | 475° C. |
| 5 | 5° C. per minute | 375° C. |
| 6 | no hold | 375° C. |
| 7 | 50° C. per minute | 20° C. |
| 8 | end | |

The outer half inch or so of the partially annealed disk 10 is then removed leaving a working piece 20 with a first surface 30 that is 3 ½ inches in diameter, as shown by dimension B in FIG. 1. From this working piece 20, a 20 mm strip is cut along first cut lines (e.g., using a diamond saw blade) as shown in FIG. 2. From this strip a smaller 10 mm strip is cut along second cut lines that are perpendicular to the first cut lines as shown in FIG. 2 to create a rectangular parallelepiped 35, as shown in FIG. 3. The second cut lines define the measurement distance for the standard tool. The measurement distance may be selected for a particular type of stress analysis device or a nominal distance may be selected that is useable in various devices.

The opposing faces C and D at the top and bottom of the rectangular parallelepiped 35 in FIG. 3 are polished and the four remaining faces are marked (indicated by the cross-hatching) to insure that measurements are taken in proper direction, such as by painting them black. Note that the two opposing faces C and D are perpendicular to the first surface 30 of the working piece 20. Polishing the faces with silicon carbide papers (20, 15, 12 and 8 microns) with water as a lubricant worked well.

The birefringence of the rectangular parallelepiped 35 is then measured using a calibrated device. In this embodiment, the measured birefringence for the 10 mm measurement distance was 79.8 nm.

A set of these standard tools may be provided from the same working piece by making further second cuts at different measurement distances. For example, a set of tools with measurement distances of 2, 4, 6, 8, 10, and 12 mm can be provided by making further second cuts at each of these distances. The birefringence of each of these tools may be separately determined, but the preferred technique is to measure one and use a ratio of measurement distances to determine the rest. For example, if the 10 mm measured birefringence is 79.8, the birefringence X of each of the 2, 4, 6, 8, and 12 mm tools can be determined by X=(79.8/10)×measurement distance.

A second embodiment of the invention uses a soda-lime tempered safety glass sheet 40 such as shown in FIG. 4 (e.g., the sheet is 10 inches square and is 3/16 inches thick). The sheet is partially annealed using the following schedule:

| Step | Ramp | Temperature |
| --- | --- | --- |
| 1 | 20° C. per minute | 460° C. |
| 2 | no hold | 460° C. |
| 3 | 5° C. per minute | 475° C. |
| 4 | hold 13 minutes | 475° C. |
| 5 | 5° C. per minute | 375° C. |
| 6 | no hold | 375° C. |
| 7 | 50° C. per minute | 20° C. |
| 8 | end | |

The outer 1 ½ inches or so of the partially annealed sheet 40 is then removed leaving a working piece 50 with a first surface 60 that is 7 inches across, as shown in FIG. 4. As in the first embodiment, a 20 mm strip is cut from working piece 50 as shown in FIG. 5. From this strip a smaller 10 mm strip is cut to create a rectangular parallelepiped 65, as shown in FIG. 6.

The opposing faces C and D at the top and bottom of the rectangular parallelepiped 65 of FIG. 6 are polished and the four remaining faces are marked as discussed above. As with the first embodiment, note that the two opposing faces C and D are perpendicular to a first surface 60 of the working piece 50.

The birefringence of the rectangular parallelepiped is then measured using a calibrated device. In this embodiment, the measured birefringence for the 10 mm measurement distance was 129.6 nm. As noted above, a set of these standard tools may be provided from the working piece by making the second cut at different measurement distances.

The starting piece of tempered glass may have sizes and shapes other than those in these embodiments, which are offered by way of example. Further, the distances for the first and second cuts may be adjusted as needed for a particular stress analysis device.

While embodiments of the present invention have been described in the foregoing specification and drawings, it is to be understood that the present invention is defined by the following claims when read in light of the specification and drawings.

What is claimed is:

1. A method of making a standard tool for calibrating devices that analyze stress in photoelastic material, the method comprising the sequential steps of:
    partially annealing a starting piece of tempered glass, the starting piece having a first thickness and a first surface with a first dimension that is perpendicular to the first thickness;
    removing a peripheral portion of the partially annealed starting piece to leave a working piece having the first thickness and a second dimension less than the first dimension;
    cutting a rectangular parallelepiped from the working piece;
polishing two opposing faces of the rectangular parallelepiped, the two opposing faces being spaced apart by a measurement distance through which light passes during stress analysis in a stress analysis device, the two opposing faces being perpendicular to the first surface; and
    determining a birefringence of the rectangular parallelepiped across the measurement distance using a calibrated stress analysis device, the rectangular parallelepiped being the standard tool that has the determined birefringence for the measurement distance.

2. The method of claim 1, wherein the second dimension is less than 80% of the first dimension.

3. The method of claim 1, wherein the step of partially annealing causes said partially annealed starting piece to have retardance below 250 nm/cm.

4. The method of claim 1, further comprising a step of marking four remaining faces of the rectangular parallelepiped to avoid using the four remaining faces when calibrating stress analysis devices.

5. The method of claim 4, wherein the marking step comprises the step of blackening the four remaining faces.

6. The method of claim 1, wherein the step of partially annealing the starting piece of tempered glass comprises the steps of heating an oven containing the starting piece of tempered glass from ambient temperature to a first temperature range of 400-500° C. at a first rate, holding the oven temperature to within the first temperature range for a predetermined time, cooling the oven to a second temperature range of 300-400° C. at a second rate slower than the first rate, and then cooling the oven to ambient temperature at a third rate faster than the first rate.

7. The method of claim 6, wherein the first rate is about 20° C./min, the second rate is about 5° C./min, and the third rate is about 50° C./min.

8. The method of claim 7, wherein after heating the oven, the oven temperature is held at about 475° C. for 10-15 minutes.

9. The method of claim 1, further comprising a step of making a set of the standard tools by cutting further rectangular parallelepipeds from the working piece and polishing respective opposing faces thereof, wherein each of the further rectangular parallelepipeds has a different respective measurement distance.

10. The method of claim 1, wherein the cutting step comprises the steps of making first cuts at a first distance apart and thereafter making second cuts at a second distance apart and perpendicular to the first cuts, the second distance defining the measurement distance.

11. The method of claim 10, wherein the first distance is about 20 mm and the second distance is in a range of 2 to 12 mm.

12. A method of making a set of standard tools for calibrating a polarimeter, the method comprising the sequential steps of:
    partially annealing a starting piece of tempered glass to the strain point of the glass so that the partially annealed starting piece has a retardance below 250 nm/cm, the starting piece having a first thickness and a first surface with a first dimension, the first thickness being perpendicular to said first surface;
    removing a peripheral portion of the first surface to leave a working piece having the first thickness and a second dimension that is less than the first dimension;
    cutting plural rectangular parallelepipeds from the working piece, each of the rectangular parallelepipeds having two opposing faces spaced apart by a different respective measurement distance through which light passes during stress analysis in a polarimeter, the two opposing faces being perpendicular to the first surface;
    polishing the two opposing faces of the rectangular parallelepipeds; and
    determining a birefringence of each of the rectangular parallelepipeds, the rectangular parallelepipeds being the set of standard tools that have the respectively determined birefringence for the respective measurement distances.

13. The method of claim 12, wherein the step of determining the birefringence comprises the steps of measuring a birefringence of one of the rectangular parallelepipeds across the respective measurement distance using a calibrated polarimeter, and determining a birefringence of each of the other rectangular parallelepipeds based on a ratio of the respective measurement distance to the measurement distance of the one rectangular parallelepiped.

14. The method of claim 12, further comprising the step of blackening four faces of each of the rectangular parallelepipeds other than the two opposing faces.

15. The method of claim 12, wherein the cutting step comprises the steps of making first cuts at a first distance apart and thereafter making plural pairs of second cuts that are each a respective second distance apart and perpendicular to the first cuts, the second distance defining the measurement distance.

16. The method of claim 15, wherein the measurement distance is in a range of 2 to 12 mm.

17. A set of standard tools for calibrating a polarimeter, the set comprising:
plural separate rectangular parallelepipeds that are made of partially annealed tempered glass with a retardance below 250 nm/cm, each of said rectangular parallelepipeds having two opposing polished faces spaced apart by a different respective measurement distance through which light passes during stress analysis in a polarimeter,
four faces of each of said rectangular parallelepipeds, other than said two opposing faces, being blackened,
each of said rectangular parallelepipeds having a known birefringence for the respective measurement distance.

18. The set of claim 17, wherein the measurement distance is in a range of 2 to 12 mm.

* * * * *